United States Patent [19]

Rausch et al.

[11] Patent Number: 6,100,416
[45] Date of Patent: Aug. 8, 2000

[54] ASYMMETRIC ETHYLENE-BRIDGED METALLOCENES USEFUL AS CATALYSTS IN THE POLYMERIZATION OF OLEFINS AND PROCESS FOR PREPARING SAID METALLOCENES

[75] Inventors: Marvin D. Rausch; Emma J. Thomas, both of Amherst, Mass.; Serge Bettonville, Crisnee; Didier Grandfils, Brussels, both of Belgium

[73] Assignee: Solvay Polyolefins Europe-Belgium (Société Anonyme), Brussels, Belgium

[21] Appl. No.: 09/087,981

[22] Filed: Jun. 1, 1998

[51] Int. Cl.[7] ............................. C07F 17/00; C07F 7/00
[52] U.S. Cl. ....................... 556/53; 502/103; 502/117; 526/160; 526/943
[58] Field of Search .................. 556/53; 502/103, 502/117; 526/160, 943

[56] References Cited

U.S. PATENT DOCUMENTS 5,391,789  2/1995  Rohrmann ............................... 556/11

FOREIGN PATENT DOCUMENTS

0754698A2  1/1997  European Pat. Off. .

OTHER PUBLICATIONS

"Unisymmetric ansa–Zirconocene Complexes with Chiral Ethylene Bridges: Influence of Bridge Conformation and Monomer Concentration on the Stereoselectivity of the Propene Polymerization Reaction" by B. Rieger et al. Organometallics 1994, 13, 647–653.

Primary Examiner—Porfirio Nazario-Gonzalez
Attorney, Agent, or Firm—Venable; John W. Schneller

[57] ABSTRACT

Novel asymmetric ethylene-bridged metallocenes useful as catalysts in the polymerization of olefins and process for preparing said metallocenes.

The novel metallocenes are represented by the general formula:

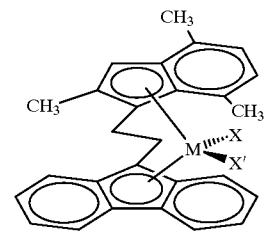

wherein M represents a transition metal selected from titanium, zirconium and hafnium and X and X' represent a halogen atom. Preferably, the transition metal is Zr and the halogen atoms are both chlorine.

Process for producing the novel metallocenes of general formula (I) comprising the steps of:

a) reacting fluorenyllithium with 1,2-dibromoethane to produce 1-(9-fluorenyl)-2-bromoethane, b) reacting the said 1-(9-fluorenyl)-2-bromoethane with 2,4,7-trimethylindenyllithium to produce 1-(9-fluorenyl)-2-[1-(2,4,7-trimethyl)indenyl]ethane precursor, c) reacting the said 1-(9-fluorenyl)-2-[1-(2,4,7-trimethyl)indenyl]ethane precursor with butyllithium to produce its dilithium salt and d) reacting the said dilithium salt with a transition metal halide selected from halides of Ti, Zr and Hf to produce the metallocenes.

The novel metallocenes are useful as catalysts for the polymerization of olefins such as ethylene and propylene and, in particular, for the production of higly isotactic polypropylene.

14 Claims, No Drawings

ASYMMETRIC ETHYLENE-BRIDGED METALLOCENES USEFUL AS CATALYSTS IN THE POLYMERIZATION OF OLEFINS AND PROCESS FOR PREPARING SAID METALLOCENES

TECHNICAL FIELD

The present invention relates to novel asymmetric ethylene-bridged metallocenes useful as catalysts for the polymerization of olefins. It relates more specifically to novel ethylene-bridged metallocenes containing fluorenyl and indenyl fragments. It also relates to a process for the preparation of said asymmetric ethylene-bridged metallocenes.

BACKGROUND OF THE INVENTION

Some asymmetric ethylene-bridged metallocenes derived from group 4 metals and containing fluorenyl and indenyl fragments have already been proposed for the polymerization of olefins such as propylene (EP-A-0 754 698).

However, most of them lead to poor isotacticity. It is so that 1-($\eta^5$-9 fluorenyl)-2-[$\eta^5$-1-(2-methyl)indenyl]ethane zirconium dichloride used in combination with aluminoxanes (MAO) produces polypropylene having a limited stereospecificity (about fifty mole % mm triads) and a rather low melting point. On the other hand, the 1-($\eta^5$-9-fluorenyl)-2-[$\eta^5$-1-(4,7-dimethyl)indenyl]ethane zirconium chloride, when used in combination with MAO, produces a purely atactic polypropylene (mm triads about 25%) characterized by the absence of any melting point.

Ethylene-bridged indenyl fluorenyl metallocenes are generally produced by a route comprising the reaction of fluorenyllithium with ethylene oxide to form 9-hydroxyethylfluorene which in turn is reacted with 1 equivalent of trifluoromethanesulfonic acid anhydride to replace the hydroxyl group by a —OSO2CF3 group; the said sulfoderivative being finally reacted with 1,2 equivalent indenyllithium to produce the 1-(9-fluorenyl)-2-(1-indenyl) ethane metallocene precursor (B. Rieger et al., Organometallics, 1994, 13, 647–653).

This known synthesis route for ethylene-bridged indenyl fluorenyl metallocene precursors has the following drawbacks: it does require the use of excess of indene, the use of ethylene oxide and the fluorenyl intermediate (triflate) is unstable and thus not isolable.

SUMMARY OF THE INVENTION

It is an object of the present invention to solve the above problems by providing novel metallocenes useful as catalysts for olefin polymerization which are, in particular, able to produce higly isotactic polypropylene. It is another object of the present invention to provide a process for preparing said novel metallocenes.

The invention is thus related to novel metallocenes represented by the general formula (I)

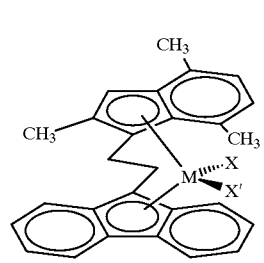

wherein M represents a transition metal selected from Ti, Zr and Hf, and X and X' represent a halogen atom.

The invention also relates to a process for the preparation of metallocenes represented by the general formula (I) comprising the following steps:
a) production of 1-(9-fluorenyl)-2-bromoethane starting from fluorenyllithium and 1,2-dibromoethane,
b) production of 1-(9-fluorenyl)-2-[1-(2,4,7-trimethyl) indenyl]ethane precursor starting from the said 1-(9-fluorenyl)-2-bromoethane and 2,4,7-trimethylindenyllithium,
c) production of the dilithium salt of the 1-(9-fluorenyl)-2-[1-(2,4,7-trimethyl)indenyl]ethane precursor and
d) production of the metallocene by reacting the said dilithium salt with a halide of a transition metal.

DETAILED DESCRIPTION

According to a first aspect, the present invention relates to novel metallocenes of the above general formula (I) wherein M represents a transition metal selected from Ti, Zr and Hf, and X and X' represent a halogen atom, i.e. 1-($\eta^5$-9-fluorenyl)-2-[$\eta^5$-1-(2,4,7-trimethyl)indenyl]ethane metallocenes.

Preferably the transition metal is selected from hafnium and zirconium. Most preferably the transition metal is zirconium.

The halogen atoms may be chosen amongst chlorine, iodine, fluorine and bromine atoms. Preferably the halogen atoms are chlorine or bromine atoms and most preferably they are both chlorine atoms. A most preferred metallocene according to the present invention is thus 1-($\eta^5$-9-fluorenyl)-2-[$\eta^5$-1-(2,4,7-trimethyl)indenyl]ethane zirconium dichloride.

Contrary to similar known substituted ethylene-bridged metallocenes containing fluorenyl and indenyl fragments, the said novel metallocenes are able to produce highly isotactic polypropylene when used in combination with a cocatalyst, such as for exemple aluminoxane.

According to a second aspect, the present invention relates to a process for producing the novel metallocenes of general formula (I).

The said process comprises the following steps:
a) reacting fluorenyllithium with 1,2-dibromoethane to produce 1-(9-fluorenyl)-2-bromoethane,
b) reacting the said 1-(9-fluorenyl)-2-bromoethane with 2,4,7-trimethylindenyllithium to produce 1-(9-fluorenyl)-2-[1-(2,4,7-trimethyl)indenyl]ethane precursor,
c) reacting the said 1-(9-fluorenyl)-2-[1-(2,4,7-trimethyl) indenyl]ethane precursor with butyllithium to produce its dilithium salt and
d) reacting the said dilithium salt with a transition metal halide selected from halides of Ti, Zr and Hf to produce the metallocenes.

Preferably, step a) is carried out with a large excess of 1,2-dibromoethane which may be as high as 25 moles per mole of fluorenyllithium.

Preferably, step b) is carried out by reacting 1-(9-fluorenyl)-2-bromoethane with 2,4,7-trimethylindenyllithium in equivalent quantity.

Preferably, step (c) is carried out by reacting 1-(9-fluorenyl)-2-[1-(2,4,7-trimethyl)indenyl]ethane precursor with two equivalents of butyllithium and step d) by reacting the dilithium salt with one equivalent of transition metal halide.

In general, steps a), b), c) and d) are carried out in inert solvents at temperatures not exceeding room temperature.

Preferably, reaction step a) is carried out in an inert solvent, such as for example tetrahydrofuran, at a temperature in the range of about 0° C. to about room temperature. At the end of reaction, the solvent and the excess of 1,2-dibromoethane are removed in order to separate the produced 1-(9-fluorenyl)-2-bromoethane which is a stable yellow solid having a melting point of 48–49° C.

Preferably, the second step (step b) is carried out in an inert solvent, such as for example tetrahydrofuran, at a low temperature which is often below to 0° C., such as for example at about −10° C. At the end of reaction, after removal of the solvent, the 1-(9-fluorenyl)-2-[1-(2,4,7-trimethyl)indenyl]ethane precursor is isolated as a white solid having a melting point of 178–179° C.

Preferably, the third step (step c) is effected in an inert solvent, such as diethyl ether at low temperature, often at a temperature around 0° C., and the resulting Li salt separated from the solvent and washed prior to being reacted, in the fourth step (step d), in an inert solvent, such as diethyl ether, with one equivalent of a transition metal halide selected from halides of Ti, Zr and Hf.

After removal of the solvent, a solid metallocene is isolated which is kept at a temperature beneath 0° C.

Preferably, the transition metal is zirconium and preferably the halide is chloride.

In the case where zirconium tetrachloride is used in step (d), the isolated metallocene is 1-($\eta^5$-9-fluorenyl)-2-[$\eta^5$-1-(2,4,7-trimethyl)indenyl]ethane zirconium dichloride which is an orange solid.

The novel metallocenes according to the present invention are useful as catalysts for the polymerization of olefins. They can be used in combination with one another. They can also be used in combination with aluminoxanes. Methylalumi-noxane is preferred. They can also be used in combination with an ionizing agent. This ionizing agent can be chosen from the compounds comprising a first part which has the properties of a Lewis acid and which is capable of ionizing the metallocene and a second part which is inert towards the ionized metallocene. Examples of ionizing agents are triphenylcarbenium tetrakis(pentafluorophenyl)borate, N,N'-dimethyl anilinium tetrakis(pentafluorophenyl)borate, tri(n-butyl)ammonium tetrakis(pentafluorophenyl)borate, tri(pentafluorophenyl)boron, triphenylboron, trimethylboron, tri(trimethylsilyl)borate and organoboroxines.

Organometallic compounds are generally used as cocatalysts and/or poison scavenger. They can be selected from organometallic compounds of lithium, magnesium, zinc, aluminium or tin. The best results are obtained with organoaluminium compounds and in particular with trialkylaluminium compounds.

The olefins can be chosen from those containing up to 20, preferably up to 12 carbon atoms per molecule. The olefin is preferably ethylene or propylene.

The novel metallocenes according to the present invention may be used for the homopolymerization of one of these olefins or for the copolymerization—random or block copolymerization—of one of these olefins with one or more comonomers. The preferred comonomers of ethylene are butene, hexene and their mixtures. The preferred comonomers of propylene are ethylene, butene and their mixtures.

The novel metallocenes according to the invention are particularly well adapted to the polymerization of propylene in order to produce highly isotactic polypropylene.

EXAMPLES

In addition to the foregoing description of the invention, the following examples are provided to further illustrate the present invention.

1. Preparation of Metallocenes

General procedure. Reactions are carried out under an argon atmosphere. Toluene, diethyl ether, tetrahydrofuran (THF) and pentane were distilled from Na/K alloy under argon. Dichloromethane was distilled from $CaH_2$ under argon. $^1H$ NMR spectra were recorded on a AC-200 spectrometer. $^{13}C$ NMR spectra were recorded on DPX 300/AMX500 spectrometer.

Example 1

This example concerns the preparation of 1-($\eta^5$-9-fluorenyl)-2-[$\eta^5$-1-(2,4,7-trimethyl)indenyl]ethane zirconium dichloride.

Step a) Preparation of 1-(9-fluorenyl)-2-bromoethane

To a solution of 10.38 g (62.5 mmol) of fluorene in 250 ml of THF at 0° C. was added dropwise a 1.6 molar solution of butyllithium in hexane (39.05 ml, 62.5 mmol) in order to produce fluorenyllithium. The solution was stirred for 3 h at room temperature and then added dropwise over a period of 2 h via a cannula to 125 ml (1.45 mol) of 1,2-dibromoethane. The solution was stirred overnight at room temperature. After hydrolysis with 125 ml aqueous $NH_4Cl$, the organic layer was separated. The aqueous layer was extracted twice with ether. The combined organic layers were dried on $MgSO_4$, filtered and the solvents were removed. The excess 1,2-dibromoethane was recovered by trap to trap distillation at 0.5 mm Hg with gentle heating by a warm water bath. A chilled receiving flask was used. The resulting yellow residue was dissolved in pentane, filtered, concentrated and cooled to −20° C. to give 1-(9-fluorenyl)-2-bromoethane (10.25 g, 60%) as a yellow solid; melting point: 48–49° C. $^1H$ NMR data was consistent with that reported in literature.

Step b) Preparation of 1-(9-fluorenyl)-2-[1-(2,4,7-trimethyl)indenyl]ethane precursor To a solution of 2,4,7-trimethylindene (2.90 g, 18.3 mmol) in 50 ml of THF at 0° C. was added dropwise a 1.6 molar solution of butyllithium in hexane (11.45 ml, 18.3 mmol) in order to produce 2,4,7-trimethylindenyllithium. The solution was stirred for 6 h at room temperature and then added via a cannula to a solution of 1-(9-fluorenyl)-2-bromoethane (5.00 g, 18.3 mmol) in 30 ml THF cooled at −10° C. The mixture was stirred overnight at room temperature and then hydrolyzed with 50 ml of aqueous $NH_4Cl$. The organic phase was separated and the aqueous layer was extracted with ether. The combined organic phases were dried on $MgSO_4$, filtered and the solvent was removed. The residue was crystallized from hot 100% ethanol to give 1.86 g (29%) of 1-(9-fluorenyl)-2-[1-(2,4,7-trimethyl)indenyl]ethane precursor as a white solid; melting point 178–179° C. $^1H$ NMR ($CDCL_3$): δ 7.77–7.28 (m, 8 H, Flu arom H), 6.96–6.74 (dd, 2 H, Ind arom H), 6.55 (s, 1 H, Ind $C_5$ vinylic H), 3.86–3.83 (t, 1 H, Flu-$C_5$ H), 3.15 (s, 1 H, Ind-C-1 H), 2.36 (s, 3 H, $CH_3$), 2.03 (s, 3 H, $CH_3$), 1.88 (s 3 H, $CH_3$)

1.66–1.23 (m, 4 H, bridge). Ms: M/z 350 (M$^+$). Anal. Calcd for $C_{27}H_{26}$: C, 92.52; H, 7.48. Found: C,92.03; H, 7.32.

Step c) Preparation of the dilithium salt of 1-($\eta^5$-9-fluorenyl)-2-[$\eta^5$-1-(2,4,7-trimethyl)indenyl]ethane precursor.

To a solution of 1-(9-fluorenyl)-2-[1-(2,4,7-trimethyl)indenyl]ethane precursor (1.35 g, 3.85 mmol) in 50 ml of diethyl ether at 0° C. was added 2 equivalents of 1.6 molar butyllithium (4.81 ml, 7.7 mmol) in order to produce the dilithium salt of 1-($\eta^5$-9-fluorenyl)-2-[$\eta^5$-1-(2,4,7-trimethyl)indenyl]ethane precursor. The resulting suspension was stirred 6 h at room temperature. The solvent was removed and the solid washed with 2×20 ml portions of pentane.

Step d): Preparation of 1-($\eta^5$-9-fluorenyl)-2-[$\eta^5$-1-(2,4,7-trimethyl)indenyl]ethane zirconium dichloride.

The washed solid issued from step c) (dilithium salt) was suspended in 60 ml of diethyl ether and cooled to 0° C. $ZrCl_4$ (1.90 g, 3.85 mmol) was added as a solid. The mixture was stirred overnight at room temperature, and the solvent was removed by filtration. The orange solid was extracted with $CH_2Cl_2$, concentrated and stored at −20° C. to give 1-($\eta^5$-9-fluorenyl)-2-[$\eta^5$-1-(2,4,7-trimethyl)indenyl]ethane zirconium dichloride (0.40 g, 20%).

$^1$H NMR (CDCl$_3$): δ 7.93–7.10 (m, 8 H, Flu arom H), 6.74–6.68 (m, 2 H, Ind arom H), 6.25 (s, 1 H, Ind-C$_5$ H), 4.54–3.94 (m, 4 H, bridge), 3.06 (s, 3 H, CH$_3$), 2.29 (s, 3 H, CH$_3$), 2.17 (s, 3 H, CH$_3$). Ms: m/z 508 (M$^+$). Anal. Calcd for $C_{27}H_{22}Cl_2Zr$: C, 63.51; H, 4.74. Found: C, 61.76 H, 4.61.

Example 2 (Reference)

Following the procedure of steps a) to d) of example 1, 1-($\eta^5$-9-fluorenyl)-2-[$\eta^5$-1-(2-methyl)indenyl]ethane zirconium dichloride (0.9 g, 38%) was prepared using 2-methylindenyllithium instead of 2,4,7-trimethylindenyllithium in step b). It is an orange solid.

$^1$H NMR (CDCl$_3$): δ 7.90–6.97 (m, 12 H, arom), 6.22 (s, 1 H, Ind-C$_5$ H), 4.72–3.75 (m, 4 H, bridge), 2.20 (s, 3 H, CH$_3$). Anal. Calcd for $C_{25}H_{20}Cl_2Zr$: C, 62.22; H, 4.18. Found: C, 62.09; H, 4.15.

Example 3 (Reference)

Following the procedure of steps a) to d) of example 1, 1-($\eta^5$-9-fluorenyl)-2-[$\eta^5$-1-(4,7-dimethyl)indenyl]ethane zirconium dichloride (0.5 g, 23%) was prepared using 4,7-dimethylindenyllithium instead of 2,4,7-trimethylindenyllithium in step b). It is a yellow/orange solid.

$^1$H NMR (CDCl$_3$): δ 7.99–7.36 (m, 8 H, Flu arom H), 6.73–6.64 (m, 2 H, Ind arom H), 6.42–6.41 (d, 2 H, Ind-C$_5$ H), 5.32 (s, 0.2 H, CH$_2$Cl$_2$), 4.52–3.71 (m, 4 H, bridge), 2.60 (s, 3 H, CH$_3$), 2.26 (s, 3 H, CH$_3$). Anal. Calcd for $C_{26}H_{22}Cl_2Zr \cdot 0.1\ CH_2Cl_2$: C, 62.07; H, 4.43. Found: C, 61.71; H, 4.34.

2. Polymerization of Olefins

General procedure for examples 4 to 8. A 250 ml crown capped glass pressure reactor containing 50 ml of toluene was equilibrated with the appropriate monomer and pressure at the desired temperature. The desired amount of methylaluminoxane (MAO) was added and the solution was stirred for 5 min. 1 ml of the appropriate metallocene catalyst solution in toluene was added and the mixture was stirred until the desired reaction time was reached.

The mixture was quenched with 2% HCl in methanol, filtered and dried in a vacuum oven at an appropriate temperature for the polymer sample.

Melting points were determined by DSC with a Perkin-Elmer DSC-System. $^{13}$C NMR spectra were determined on a DPX300 spectrometer in CDCl$_3$ at room temperature, and at 80° C. in C$_6$D$_5$Cl.

Example 4

This example is related to ethylene polymerization with the metallocene catalyst of example 1 (invention) according to the general procedure described hereabove.

The polymerization conditions were the following:

Zr=5 μmol

Al/Zr=4000:1 (molar ratio)

duration: 6 min temperature: 50° C.

pressure: 15 psi

The results of polymerization were the following:

yield: 0.661 g activity: 9.6×10$^7$ g polyethylene/(mol Zr.[C$_2$].h)

Examples 5 to 8

These examples are related to propylene polymerization according to the general procedure described hereabove. Examples 5 and 6 concern propylene polymerization with the metallocene catalyst of example 1 (invention) at 20° C., respectively at 70° C. Example 7 (reference example) concerns propylene polymerization with the metallocene catalyst of reference example 2 at 70° C. and reference example 8 concerns propylene polymerization with the metallocene catalyst of reference example 3 at 70° C.

The polymerization conditions were the following:

Zr=50 μmole

Al/Zr=4000:1 (molar ratio)

duration: 60 min pressure: 30 psi

The results of polymerization are summarized in Table I wherein the following symbols are used:

A=activity expressed in g polypropylene/(mol Zr.[C$_3$].h)

Tm(° C.)=melting temperature isotacticity, mol %=[mmmm] determined by $^{13}$C at 80° C. in C$_6$D$_5$Cl Example 9

This example is related to propylene bulk polymerization according to the following general procedure: the polymerization run is carried out in a 5 liters stainless steel reactor. Cocatalyst (MAO, 10% by weight in toluene, 45 ml), catalyst (5 μmol Zr in precontact with 5 ml MAO, 10% by weight in toluene) and liquid propylene (3,5 liters) are successively introduced under nitrogen blanket and heated to the polymerization temperature. The polymerization conditions are maintained for 60 minutes. The polymerization is then stopped by simultaneously flashing the residual monomer and cooling down the reactor.

The polymerization conditions were the following:

Zr=5 μmol

Al/Zr=15,000 (molar ratio)

duration: 60 min temperature: 70° C.

The results of polymerization were the following:

yield: 660 g activity: 132,000 g polypropylene/mmol Zr melting temperature: 151.2° C.

Isotacticity [mmmm]: 91 mol %

The examples 4, 5 and 6 and 9 demonstrate that the novel metallocenes according to the present invention are effective and productive catalysts for the polymerization of olefins such as ethylene and propylene. Comparison of the results of example 6 according to the invention with those of reference examples 7 and 8 demonstrate the superiority of the metallocenes according to the invention in regard of stereospecificity of the produced polypropylene, as well as in regard of yield and activity.

TABLE 1

| No. of example | Yield, g | A | Tm, ° C. | Isotacticity, mol % |
|---|---|---|---|---|
| 5 | 17 | $1.40 \times 10^7$ | 132 | 86 |
| 6 | 8.5 | $4.80 \times 10^7$ | 124 | 80 |
| 7 (R) | 5.3 | $3.02 \times 10^7$ | ca. 80 | 48 |
| 8 (R) | 2.0 | $1.10 \times 10^7$ | — | — |

What is claimed is:

1. A novel asymmetric ethylene-bridged metallocene useful as catalyst in the polymerization of olefins represented by the formula

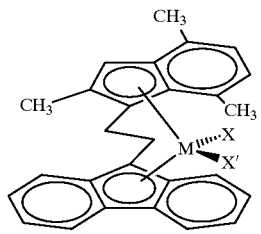

wherein M represents a transition metal selected from titanium, zirconium and hafnium and X and X' represent a halogen atom.

2. A novel asymmetric ethylene-bridged metallocene according to claim 1 wherein the transition metal is selected from hafnium and zirconium.

3. A novel asymmetric ethylene-bridged metallocene according to claim 2 wherein the transition metal is zirconium.

4. A novel asymmetric ethylene-bridged metallocene according to claim 1 wherein the halogen atoms are both chlorine atoms.

5. A novel asymmetric ethylene-bridged metallocene according to claim which is 1-($\eta^5$-9-fluorenyl)-2-[$\eta^5$-1-(2,4,7-trimethyl)indenyl]ethane zirconium dichloride.

6. A process for producing a novel ethylene-bridged metallocene comprising the following steps:

a) reacting fluorenyllithium with 1,2-dibromoethane to produce 1-(9-fluorenyl)-2-bromoethane, b) reacting the said 1-(9-fluorenyl)-2-bromoethane with 2,4,7-trimethylindenyllithium to produce 1-(9-fluorenyl)-2-[1-(2,4,7-trimethyl)indenyl]ethane precursor, c) reacting the said 1-(9-fluorenyl)-2-[1-(2,4,7-trimethyl)indenyl]ethane precursor with butyllithium to produce its dilithium salt and d) reacting the said dilithium salt with a transition metal halide selected from halides of titanium, zirconium and hafnium to produce the metallocenes.

7. Process according to claim 6, wherein the transition metal is zirconium.

8. Process according to claim 6, wherein the halogen atoms are both chlorine atoms.

9. Process according to claim 6 wherein steps a), b), c) and d) are effected in inert solvents at temperatures not exceeding room temperature.

10. A novel asymmetric ethylene-bridged metallocene produced by the process of claim 6.

11. The novel asymmetric ethylene-bridged metallocene according to claim 10, wherein the transition metal is selected from hafnium and zirconium.

12. The novel asymmetric ethylene-bridged metallocene according to claim 10, wherein the transition metal is zirconium.

13. The novel asymmetric ethylene-bridged metallocene according to claim 10, wherein the halogen atoms are both chlorine atoms.

14. The novel asymmetric ethylene-bridged metallocene according to claim 10, which is 1-($\eta^5$-9-fluorenyl)-2-[$\eta^5$-1-(2,4,7-trimethyl)indenyl]ethane zirconium dichloride.

* * * * *